(12) United States Patent
Hiller et al.

(10) Patent No.: US 9,216,052 B2
(45) Date of Patent: Dec. 22, 2015

(54) INSTRUMENT FOR THE FUSION AND CUTTING OF BLOOD VESSELS

(75) Inventors: Juergen Hiller, Dettingen (DE); Thomas Baur, Rottenburg (DE); Ralf Kuehner, Stuttgart (DE); Viktoria Rydzewski, Nuertingen (DE)

(73) Assignee: ERBE ELEKTROMEDIZIN GMBH, Tuebingen (DE)

(*) Notice: Subject to any disclaimer, the term of this patent is extended or adjusted under 35 U.S.C. 154(b) by 536 days.

(21) Appl. No.: 13/552,815

(22) Filed: Jul. 19, 2012

(65) Prior Publication Data

US 2013/0035687 A1    Feb. 7, 2013

(30) Foreign Application Priority Data

Aug. 2, 2011 (EP) .................................... 11176289

(51) Int. Cl.
*A61B 18/18* (2006.01)
*A61B 18/14* (2006.01)
*A61B 18/00* (2006.01)

(52) U.S. Cl.
CPC ............ *A61B 18/1445* (2013.01); *A61B 18/18* (2013.01); *A61B 2018/00428* (2013.01); *A61B 2018/00607* (2013.01); *A61B 2018/1455* (2013.01)

(58) Field of Classification Search
CPC ............ A61N 1/00; A61N 1/02; A61N 1/04; A61N 1/08; A61N 1/18; A61B 18/00; A61B 18/04; A61B 18/06; A61B 18/08; A61B 18/12; A61B 18/14; A61B 18/18
See application file for complete search history.

(56) References Cited

U.S. PATENT DOCUMENTS

| | | | |
|---|---|---|---|
| 6,113,598 | A | 9/2000 | Baker |
| 2002/0115997 | A1 | 8/2002 | Truckai et al. |
| 2007/0078456 | A1 | 4/2007 | Dumbauld et al. |
| 2011/0082494 | A1 | 4/2011 | Kerr et al. |

FOREIGN PATENT DOCUMENTS

DE            60226015 T2    6/2009

*Primary Examiner* — Christopher D Koharski
*Assistant Examiner* — Elizabeth K So
(74) *Attorney, Agent, or Firm* — Dickstein Shapiro LLP

(57) ABSTRACT

An instrument suitable for minimal invasive surgery. The instrument can be introduced into a body, for example, through a trocar, and has two arms and a centrally guided knife for clamping vessels. The central guidance of the knife in at least one of the arms avoids disadvantages that could otherwise develop as a result of the off-center severing of coagulated tissue. Moreover, the clean central guidance of the knife results in lower wear on the knife. Thus, a better cut quality and a longer service life of the knife can be achieved.

18 Claims, 2 Drawing Sheets

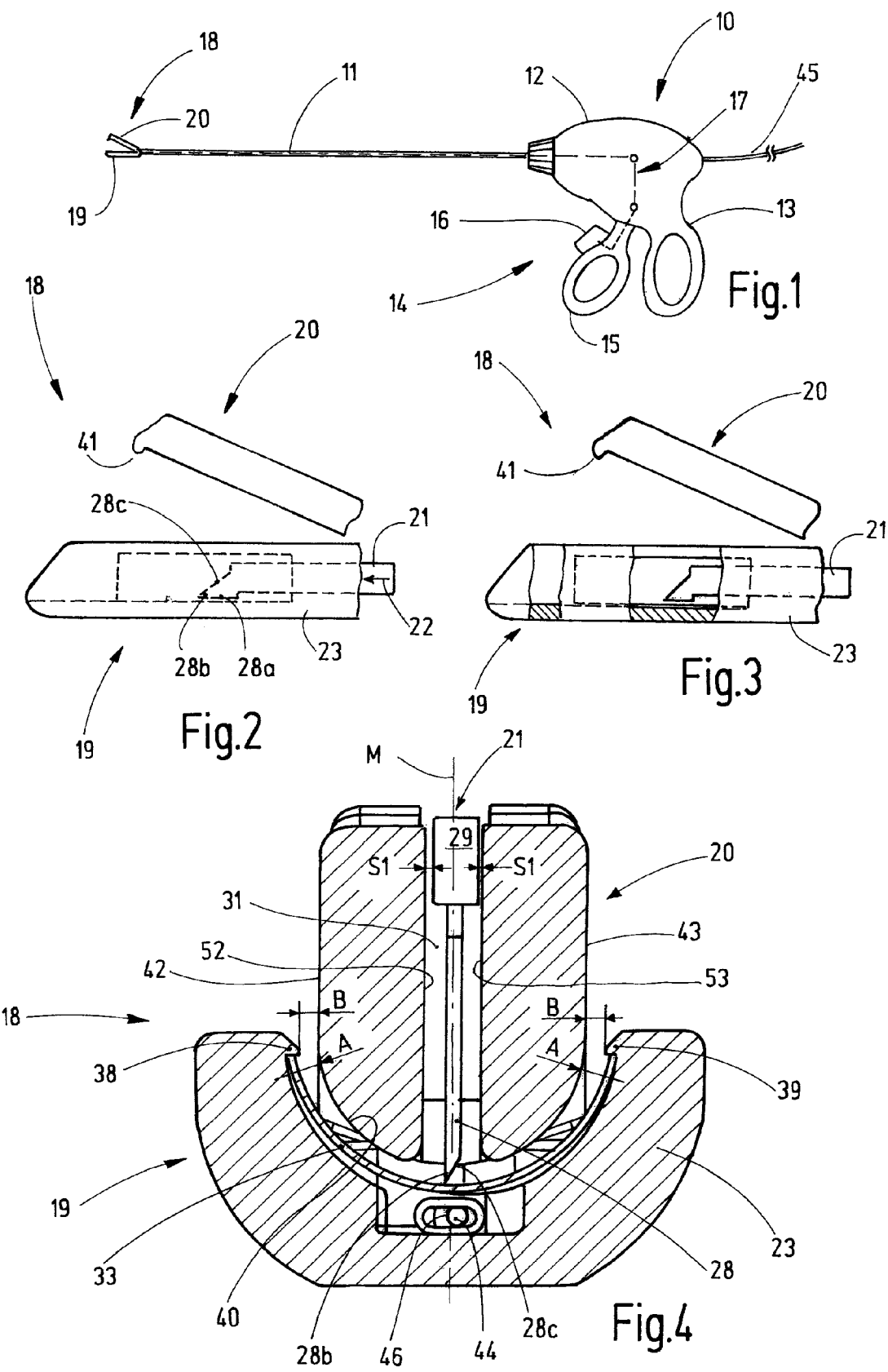

INSTRUMENT FOR THE FUSION AND CUTTING OF BLOOD VESSELS

RELATED APPLICATION

This application claims priority to European patent application EP 11 176 289.4, filed on Aug. 2, 2011, which is hereby incorporated by reference in its entirety.

TECHNICAL FIELD

Embodiments disclosed herein relate to an instrument for clamping, sealing and cutting tissue/vessels, particularly blood vessels in the living body of a human or animal patient.

BACKGROUND

Instruments for sealing and cutting blood vessels are known in principle. An example is disclosed in German publication DE 602 26 015 T2.

These instruments comprise an elongated shaft with a tool arranged at its distal end with two arms for clamping a blood vessel. In addition, a longitudinally adjustable knife is also arranged there to enable a gripped and coagulated vessel to be severed. A handle with an actuation mechanism is arranged at the proximal end of the shaft such that the arms can be closed and the knife can be actuated. The arms are designed as electrodes that can heat up the vessel clamped between them and fuse the vessel walls by coagulation.

When cutting through blood vessels, it must be ensured that the ends of the severed vessel are reliably sealed; further conditions have to be satisfied to do so. For example, any damage to surrounding tissue must be avoided. The sealing of vessels should be largely independent of the size of the vessels and the thickness of the vascular walls. Consideration must furthermore be given to the confined space available, particularly if the instrument is to be used for endoscopic or laparoscopic applications.

SUMMARY

Accordingly, an object of the embodiments disclosed herein is to create an instrument for the fusing and cutting of vessels, with which vessels can be sealed and cut to a high quality standard.

The instrument in accordance with the present disclosure is used for the sealing and cutting of blood vessels. The instrument has two arms, at least one of which is mounted such that it can be moved, desirably pivoted, relative to the other. Both arms can be mounted such that they can move relative to the shaft of the instrument. It is also possible for one of the arms to be rigidly connected to the shaft while the other is movably mounted. The latter is presently desired. The mounting of the arms can be configured such that tissue that is not uniform can be readily gripped.

The first arm has an electrically isolating base body of, for example, a ceramic or a suitable plastic, with a groove-like recess for an electrode and a guide slot for a knife. The groove-like recess is matched to the shape of the electrode. The electrode has a concave recess and can be formed as, for example, a cylindrical shell. It can, however, also have a U-cross section with straight limbs. In a further alternative, the electrode can be a flat electrode. Desirably, the electrode is formed by a thin-walled plate part that is provided with the necessary mechanical stability by bracing in the base body.

The electrode is connected via an electrical connection means to a line extending through the shaft. The connection means is desirably an isolated electrical conductor that extends through suitable channels or passages in the base body and can extend, particularly in the proximity of a joint where the second arm is movably mounted on the first arm, along the outer side of the base body, for example. The base body can be provided with a recess extending longitudinally for this purpose, inside which the line is arranged. This ensures that the head of the instrument does not exceed a maximum external cross-section and that the instrument can be pushed through a trocar, for example, for laparoscopic use.

A physiologically compatible material such as silver, titanium or the like is desirably used as the electrical conductor. The conductor can be formed as a solid round wire, hollow wire, flat wire or braid, as a strip or the like.

The knife is precisely guided at least inside the guide slot of the base body. Desirably, the knife is guided centrally to the electrode and also centrally to the second arm, into the longitudinal slot of which it can move. Upon being pushed forward, the knife can be guided at least in part by the longitudinal slot of the second arm.

The precise guidance of the knife can ensure that, when cutting through a vessel, the cut is made centrally in the previously fused region of the vessel. Thus, both ends of the severed vessel have equally long fused sections. The danger of uncontrolled bleeding due to a cut not made precisely centrally is minimized.

The knife desirably has a guide strip and a blade that are securely connected to one another. The guide strip is desirably an elongated element extending in the direction of movement of the knife, for example, in the form of a plastic rail. The strip can be connected to a blade of metal. The blade can, however, also be a ceramic, diamond, plastic or other material. The guide strip can alternatively be made of metal. It is also possible for the guide strip to be formed by a thickened portion of the blade such that the guide strip and blade form a single-part seamless unit. The two-part structure, however, is desired.

The lateral play of the knife in the guide slot and/or in the longitudinal slot is desirably less than five times the thickness D of the blade. The lateral play of the knife is desirably approximately the same as the thickness of the blade at the maximum. This enables a precise central guidance of the knife and thus, central guidance of the cut in the fused tissue region. Lateral guidance of the knife can be provided by the guide slot. Lateral guidance of the knife can alternatively be provided by the longitudinal slot. Lateral guidance is desirably provided by both the guide slot and the longitudinal slot.

The lateral play of the knife disclosed herein is understood to be the distance of the flanks of the guide strip from the flank of the guide slot or longitudinal slot with the knife in the central position. Thus, the lateral mobility of the knife corresponds to twice the play.

The knife desirably has a straight and longitudinally extending sliding edge that faces and abuts the electrode. The sliding edge can be designed relatively short and desirably directly adjoins the cutting edge of the knife. It thus ensures that the vessel gripped between the arms is severed across its entire cross-section and no residual tissue remains that is not severed.

The cutting edge is desirably arranged on the front side of the knife and is desirably at an angle to the direction of movement of the knife. This angle can be an acute angle. The cutting edge is desirably designed straight and extending in the direction of the guide strip. The guide strip desirably projects beyond the cutting edge to prevent parts of the vessel-to-be severed from being forced over the knife and thus missed by the cut.

The second arm has an electrically conducting surface, at least on its side facing the electrode. If the second arm is of a non-metallic material, then this surface can be formed by a thin electrode plate. The second arm, however, is desirably made of a solid metal. Independently thereof, the second arm has on its side facing the electrode a shape that follows the shape of the electrode. In other words, a distance gap of substantially constant gap width, or decreasing towards the middle, is formed between the electrode and the second arm. Independently thereof, the surface of the second arm can be profiled, for example, ribbed, napped or otherwise shaped. The electrode can also be provided with surface profiling. Even if the profiling of the electrode and the second arm are different, they desirably should have basic shapes that match one another and follow one another for defining a distance gap with a gap width that desirably decreases towards the middle.

The retaining means for fixing the electrode to the first arm are desirably formed on the upper edges of the recess that faces one another. These retaining means are desirably formed by electrically isolating projections that are comprised of, for example, the same material as the base body; they desirably extend in the direction of the second arm and thus cover the upper edge of the electrode. With the instrument closed, the projections desirably define a gap with the second arm with a distance B that is at a maximum as large as the width A of the distance gap in the vicinity of the retaining means.

Tissue of the vessel to be clamped off can be gripped between the second arm and the projections without coagulation due to the electrically isolating properties of the projections. Gripping of the tissue is also ensured if the arms do not close symmetrically because of tissue characteristics. If, for example, a vessel is gripped that has a cross-section that changes over its length, the lateral distances B having different values, i.e., not being the same size, can result. The vessel is nevertheless gripped securely. Slippage of the vessel is reliably ruled out even if the tissue gripped between the arm and the electrode shrinks due to the action of heat and coagulation and the clamping effect is reduced at that point. A lateral slippage of the vessel and as a consequence later severing of the vessel at an unsuitable point during subsequent activation of the knife are reliably ruled out in this way.

The retaining means formed by the projections, for example, have a dual function: they hold the electrode and they improve gripping of the vessel.

Spacing means is desirably provided between the first and the second arms. This spacing means prevents the second arm from contacting the electrode and thus prevents a short circuit. In addition, the spacing means prevents excessive pressure from being exerted unintentionally on the vessel and thereby crushing it. The spacing means is desirably formed by a metallic projection, to which is assigned a non-metallic limit stop on its opposite side. The metallic projection is desirably connected to an electrical source, i.e. it is connected to the electrode or to the second arm; this prevents unwanted errors that can occur if biological tissue gets between the projection and the assigned contact surface. If the projection is arranged in the vicinity of the counter-pole electrode, in particular, connection to an electrical source can result in a certain current flow into the gripped biological tissue so that it shrinks and no longer hinders the setting of the desired minimal distance between the second arm and the electrode. Alternatively, it is possible for the spacing means to be formed from a material that is not electrically conducting. The danger of a short circuit between the arms can thereby be reduced. This additionally enables the coagulation region to be expanded.

BRIEF DESCRIPTION OF THE DRAWINGS

Numerous variations of the aforementioned methods are possible. Hereinafter, exemplary embodiments of the invention are explained in greater detail with reference to drawings, in which:

FIG. 1 is a schematic representation of an instrument in accordance with the embodiments disclosed herein;

FIG. 2 is a schematic side view of the arms and the knife of the instrument;

FIG. 3 is a partial cutaway view of the arms and knife according to FIG. 2;

FIG. 4 illustrates the arms and the knife in a vertical sectional representation, looking in the direction of the longitudinal axis, in a simplified and schematic representation with the tool closed;

DETAILED DESCRIPTION

Figure 5:
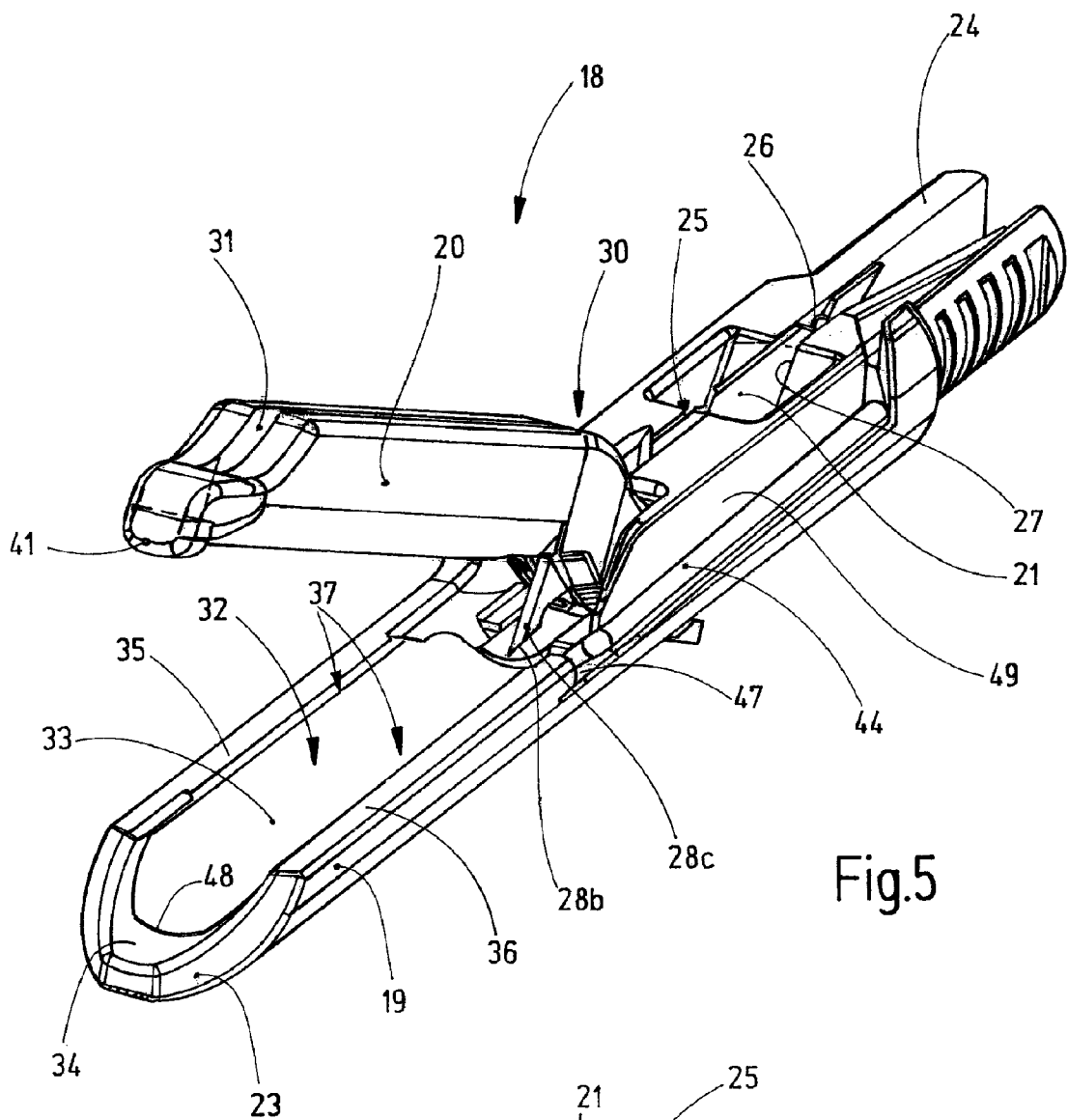
FIG. 5 is a perspective view of the head of the instrument in accordance with the embodiments disclosed herein.

FIG. 1 shows an instrument 10 that can be used, for example to clamp, fuse or sever a blood vessel when operating on a human or animal body. The instrument 10 is used, in particular, for endoscopic surgery. The instrument 10 comprises a thin shaft 11 that is held at its proximal end in a housing 12. The housing 12 has handling means, for example, a handle 13 as well as actuating elements 14. The actuating elements can comprise, for example, a pivotable handle part 15 and/or an actuating button or lever 16, as well as other elements such as, for example, electrical switches when necessary. The actuating elements 14 are connected to an application part 18 arranged on the distal end of the shaft 11 by power transfer means 17 (shown only schematically in FIG. 1 by a dot-dash line). The application part or head 18 of the surgical instrument 10 comprises at least the elements shown in FIGS. 2 and 3, namely a first arm 19, a second arm 20 and a knife 21. The arms 19, 20 are used to clamp a vessel because they can be moved towards one another to securely grip the vessel between them. The knife 21 is used to cut through the vessel.

In the present example, arm 19 is rigidly connected to the shaft 11, while arm 20 can be swiveled towards arm 19 or away from it by actuation of the handle part 15. In contrast, the knife 21 is pushed forwards in the longitudinal direction of the shaft 11 by actuation of the actuating button 16 (as shown in FIG. 2 by an arrow 22).

The arm 19 has a plurality of parts and comprises, for example, a base body 23 of plastic or ceramic (shown in more detail in FIG. 4). The base body 23 is rigidly connected at its shaft-side end to the shaft 11, for which purpose it has a shoulder 24 that can be seen in FIG. 5. The elongated base body 23 emanates therefrom and extends away from it, and has a guide slot for the knife 21. The guide slot 25 extends in a longitudinal direction through the elongated round body 23 and has two slot flanks 26, 27 that are opposite one another, separated by a distance and parallel to each other, that guide the knife 21 between them (illustrated in FIG. 6 in more detail). The knife 21 illustrated in its central position is at a distance designated as play S from each slot flank 26, 27, said distance being desirably at a maximum as great as the thickness D of the knife 21.

Figure 6:
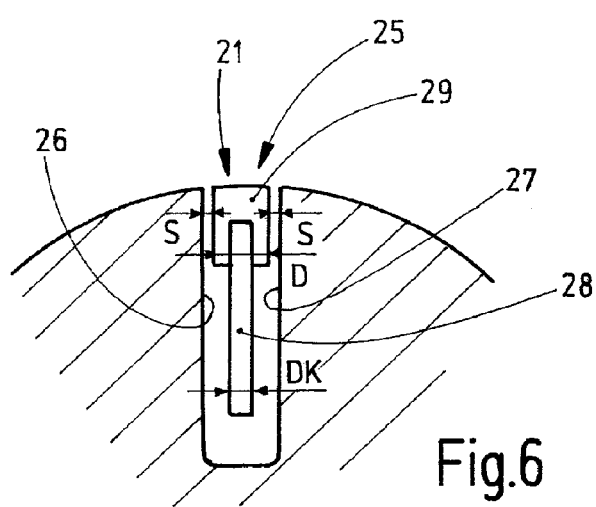
FIG. 6 illustrates the base body and knife, in a vertical sectional representation with a view in the direction of the longitudinal axis, in a simplified and schematic representation.

The knife 21 comprises a blade 28 having a guide strip 29 at its upper edge. As used herein, thickness D is the thickness of the guide strip 21 and thickness DK is the thickness of the blade 28 (FIG. 6). Play S is desirably of a value that does not exceed five times the thickness DK of the knife. In a more favorable scenario, the thickness DK of the knife is no more than twice the play S. In other words, the knife 21 can move back and forth between the flanks 26, 27 by a distance that is at a maximum two times the play S. Ideally, the thickness DK of the knife 21 is no greater than the play S.

The knife 21 desirably has a sliding edge 28a arranged, for example, on the blade 28, which can slide along the base of the arm 19 and guides the knife vertically (FIG. 2). As a result, the tip 28b of the blade 28 adjoining the cutting edge 28c (FIGS. 4 and 5) can pass along the electrode 33, or at a very short distance therefrom, without wear.

A bearing region or hinge region 30 adjoins the guide slot 25 in a straight extension, in which region the second arm 20 is mounted pivotably on the base body 23. Arm 20 is connected to power transfer means 17, not shown in detail in FIG. 5, such that it can be swiveled about an axis arranged transversely to the base body 23.

The guide slot 25 continues through arm 20 as longitudinal slot 31. The longitudinal slot 31 is open at least downwardly, i.e., in a downward direction to the bade body 23. Its width desirably corresponds at least approximately to the width of the guide slot 25. The slot flanks 52, 53 of the longitudinal slot 31 are flat surfaces oriented parallel to one another. With the knife 21, the slot, flanks 52, 53 define the play dimensions S1 (corresponding to play S).

The base body 23 has a groove-shaped or trough-shaped recess 32 below the arm 20 in which an electrode 33 is arranged. The electrode 33 is formed in the illustrated example by a thin cylindrical-dish-shaped plate. The electrode 33 has a curved, desirably concave, desirably closed, smooth surface on the side facing arm 19. The electrode 33 extends over almost the entire length of the recess 32, leaving a region 34 free at the front end of the base body 23. Retaining means 37 for the electrode 33 are arranged at the upper edges 35, 36 of the base body 23. These means 37 are, as shown in FIG. 4, formed by snap-fit projections 38, 39 comprising electrically isolating material and are desirably a one-piece component with the base body 23. The snap-fit projections 38, 39 form retaining lugs that grip over the top edge of the electrode 33. Their length desirably somewhat exceeds the thickness of the electrode 33, such that they project somewhat beyond the exposed electrode surface.

The upper arm 20 has, at its lower side facing the electrode 33, an electrode surface 40 that follows the shape of the electrode 33. If the electrode 33 has a cylindrical dish shape, for example, then the electrode surface 40 similarly follows a circular arc, having a somewhat smaller radius. Independently of this basic form, both the electrode 33 and the electrode surface 40 can have local deviations in shape in the form of recesses, projections, naps, ribs or the like.

A nose-like projection 41 extending to the base body 23 is provided at the distal end of the second arm 20 and, when the instrument is closed, is braced against the end region 34 of the base body 23. In this condition, a distance gap of width A is defined between the electrode surface 40 and the inside of the electrode 33. This width A is desirably, at least slightly, greater than the distance B between the projection 38/39 and the electrode surface 40 or the adjoining flank 42, 43 of the second arm 20.

The electrode 33, as can be seen from FIGS. 4 and 5, is connected to an electrical source via an electrical conductor 44. The conductor 44 extends through the shaft 11, firstly into the housing 12 and to a switch (not shown in detail), and to a supplying device via a feed line 45.

Similarly, a conductor, not shown in further detail, extends from the second arm 20 to the supplying device. The conductor 44 can be, for example, a round wire provided with insulation 46 or the like. The conductor 44 is connected to the electrode 33 approximately centrally at a point between the electrode 33 and the base body 23. In particular in the hinge region 30, the conductor 44 is passed through a lateral opening 47 in the base body 23 at its outer side and extends in a longitudinal recess 49 up to the shoulder 24. At that point, the conductor 44 enters the shaft 11. The conductor 44 can be, in particular, an insulated silver wire.

The instrument 10 described so far operates as follows. To seal and sever a vessel, the instrument 10 is gripped between the arms 19, 20. Actuation of the handle part 15 causes the arms 19, 20 to move towards each other such that the vessel is clamped and the vessel walls are pressed against one another. Here, the vessel walls are squeezed together, in particular, between the electrode surface 40 and the electrode 33. They are additionally gripped between the projections 38, 39 and the electrode surface 40 or the flanks 42, 43. Ideally, the projection 41 is located on the region 34 of the base body 23 acting as a thrust bearing and thus prevents crushing of the vessel.

Application of a current or voltage between the second arm 20 and the electrode 33, desirably a HF voltage, initiates a coagulation process, during the course of which cells of the vascular walls are opened and protein is released and denatured. The vascular walls gripped between the arm 20 and the electrode 33 and pressed against one another bond together. They can lose volume in the process. Independently of the shrinkage in volume of the vascular walls, the parts of the vessels gripped between the projections 38, 39 and the arm 20 remain, at least substantially, in a natural state and are thus subject to hardly any shrinkage. They remain reliably gripped, preventing lateral slippage of the vessel, which is of particular importance for the sealing of relatively small vessels.

If, however, residual tissue enters between the nose 41 and the region 34 acting as a thrust bearing, such that the gap distance A is somewhat larger than actually intended, then the narrow gap B acts as a safeguard against lateral slippage of the vessel. Moreover, the distance between the nose 41 and the front end 48 of the electrode 33 can be so small that any tissue present there coagulates and shrinks; this is also beneficial for the reliable gripping of the tissue between the arms 19, 20.

Once the coagulation process is sufficiently far advanced the surgeon can activate the knife, for example, by actuation of the button 16. The knife is now pushed, guided centrally by the guide slot 25 and the longitudinal slot 31, to the free ends of the arms 19, 20. Here, the knife 21 extends more or less precisely within a central plane M (indicated in FIG. 4 by a dot-dash line) to ensure that regions of sealed vessel ends, of equal length, result on both sides of the knife 21. The danger of an off-center cut, and hence the danger of uncontrolled bleeding, is thereby minimized.

An instrument 10 that is desirably suitable for minimal invasive surgery, which can be introduced into a body through a trocar, for example, has two arms 19, 20 and a centrally guided knife 21 for clamping vessels. The central guidance of the knife in at least one of the arms 19, 20 avoids disadvantages that could otherwise develop as a result of the off-center severing of coagulated tissue. Moreover, the clean central guidance of the knife 21 results in lower wear on it. The embodiments disclosed herein thus ensure a better cut quality and a longer service life of the knife 21.

One of the arms desirably has a ceramic base body 23 having, at its top edges, internally projecting projections 38, 39 having the form of an undercut. These electrically isolating projections extend in the direction of the central plane M and provide two improvements: on the one hand, the assembly of the electrode 33 is substantially facilitated. On the other hand, two tissue clamping points are created. The projections can be formed such that when the arms 20, 19 are closed, the distance A between the electrode formed by the upper arm 20 and the electrode 33 at the point at which the distance A has its maximum width, and the two distances B between the projections 38, 39 and the arm 20, is the same as, almost the same as, or marginally less than the distance A. This has the advantage that during the coagulation process, in which the tissue volume falls within the coagulation region, the tissue is nevertheless securely gripped. The distance A desirably tapers from the projections 38, 39 to the guide slot 31. With the present instrument, the coagulation width is determined by the isolating projections 38, 39 and is thus reliably reproducible, which substantially improves the quality of coagulation.

What is claimed is:

1. An instrument for the fusion and cutting of vessels, said instrument comprising:
   a first arm having an electrically isolating base body with a groove-like recess and a guide slot, wherein retaining means are formed on the base body for the fixed-position mounting of an electrode having a curved shape, and wherein the retaining means are formed by electrically isolating projections that project inwards in a direction of the groove-like recess and beyond an upper edge of the electrode thereby covering the upper edge of the electrode;
   a second arm movably mounted on the base body such that the second arm can move towards and away from the electrode, the second arm having a longitudinal slot; and
   a knife arranged in the guide slot of the base body such that the knife is longitudinally movable and arranged projecting into the longitudinal slot or movable into the longitudinal slot.

2. The instrument according to claim 1, wherein the knife comprises a guide strip and a blade that are securely connected to one another.

3. The instrument according to claim 2, wherein lateral play of the knife in the guide slot is less than five times the thickness of the blade.

4. The instrument according to claim 1, wherein the knife has a straight and longitudinally extending sliding edge that faces and contacts the electrode.

5. The instrument according to claim 1, wherein the knife has a cutting edge on a front side that is oriented at an angle to the direction of movement of the knife.

6. The instrument according to claim 1, wherein the knife has, on a side facing away from the electrode, a guide strip arranged longitudinally movable in the guide slot of the base body and projects into the longitudinal slot of the second arm and which determines lateral play of the knife in the base body and in the second arm.

7. The instrument according to claim 1, wherein the knife has, on a side facing away from the electrode, a guide strip arranged longitudinally movable in the guide slot of the base body and is arranged such that it can be moved into the longitudinal slot of the second arm and which determines lateral play of the knife in the base body and in the second arm.

8. The instrument according to claim 1, wherein the second arm is formed by a solid metal body.

9. The instrument according to claim 1, wherein the second arm, at a side facing the electrode of the first arm, has a shape that follows the shape of the electrode.

10. The instrument according to claim 1, wherein a distance gap with a width is defined between the electrode and the second arm when the arms are closed.

11. The instrument according to claim 1, wherein when the arms are closed, the retaining means define together with the second arm a distance that is the same or less than the width of the distance gap.

12. The instrument according to claim 1, wherein the electrode is connected to an electrical supply source via an electrical supply line arranged on the outer side of the base body.

13. The instrument according to claim 1, wherein the base body is connected to an elongated shaft that which extends away from a housing, the shaft having force transfer means for the selective movement of the second arm.

14. The instrument according to claim 1, wherein the base body is connected to an elongated shaft that which extends away from a housing, the shaft having force transfer means for the selective movement of the knife.

15. The instrument according to claim 1, wherein spacing means is provided on the first arm.

16. The instrument according to claim 15, wherein the spacing means is a metallic, electrically conducting or electrically isolating projection.

17. The instrument according to claim 1, wherein spacing means is provided on the second arm.

18. The instrument according to claim 17, wherein the spacing means is a metallic, electrically conducting or electrically isolating projection.

* * * * *